United States Patent [19]

Altman

[11] 4,286,468
[45] Sep. 1, 1981

[54] FRUSTRATED TOTAL INTERNAL REFLECTION FIBER-OPTIC SMALL-MOTION SENSOR FOR HYDROPHONE USE

[75] Inventor: Daniel E. Altman, San Diego, Calif.

[73] Assignee: The United States of America as represented by the Secretary of the Navy, Washington, D.C.

[21] Appl. No.: 72,820

[22] Filed: Sep. 4, 1979

[51] Int. Cl.³ ............................................. G01N 29/04
[52] U.S. Cl. ....................................... 73/655; 350/485
[58] Field of Search .............. 350/96.10, 96.15, 96.19, 350/96.20, 285, 485; 73/649, 653, 655; 455/612, 614

[56] References Cited
U.S. PATENT DOCUMENTS

| | | | |
|---|---|---|---|
| 3,831,137 | 8/1974 | Cuomo | 73/653 X |
| 4,132,117 | 1/1979 | Primbsch | 73/655 X |
| 4,162,397 | 7/1979 | Bucaro | 73/655 X |

*Primary Examiner*—F. L. Evans
*Attorney, Agent, or Firm*—R. S. Sciascia; Ervin F. Johnston; Thomas Glenn Keough

[57] ABSTRACT

A method and apparatus for sensing motion relies upon the total light transmitted by an optical fiber. The fiber is wound in a spiral coil and cemented to a rigid base and a portion of the fiber's cladding is removed exposing its core. A highly refractive plate is placed closely adjacent the exposed core. When the plate is displaced, it intercepts at least a portion of the evanescent field that is adjacent to the spiral core. The intercepted portion reduces the total amount of light otherwise projected through the coiled optic fiber so that a detector can provide representations of the amplitude and frequency of the plate motion. The plate only penetrates the fiber's evanescent optical field which is associated with the total internal reflection at the glass-to-air interface at the fiber's surface. Adjusting devices and pressure compensation optionally are employed making this device suitable for use has a hydrophone.

10 Claims, 3 Drawing Figures

U.S. Patent　　　Sep. 1, 1981　　　4,286,468
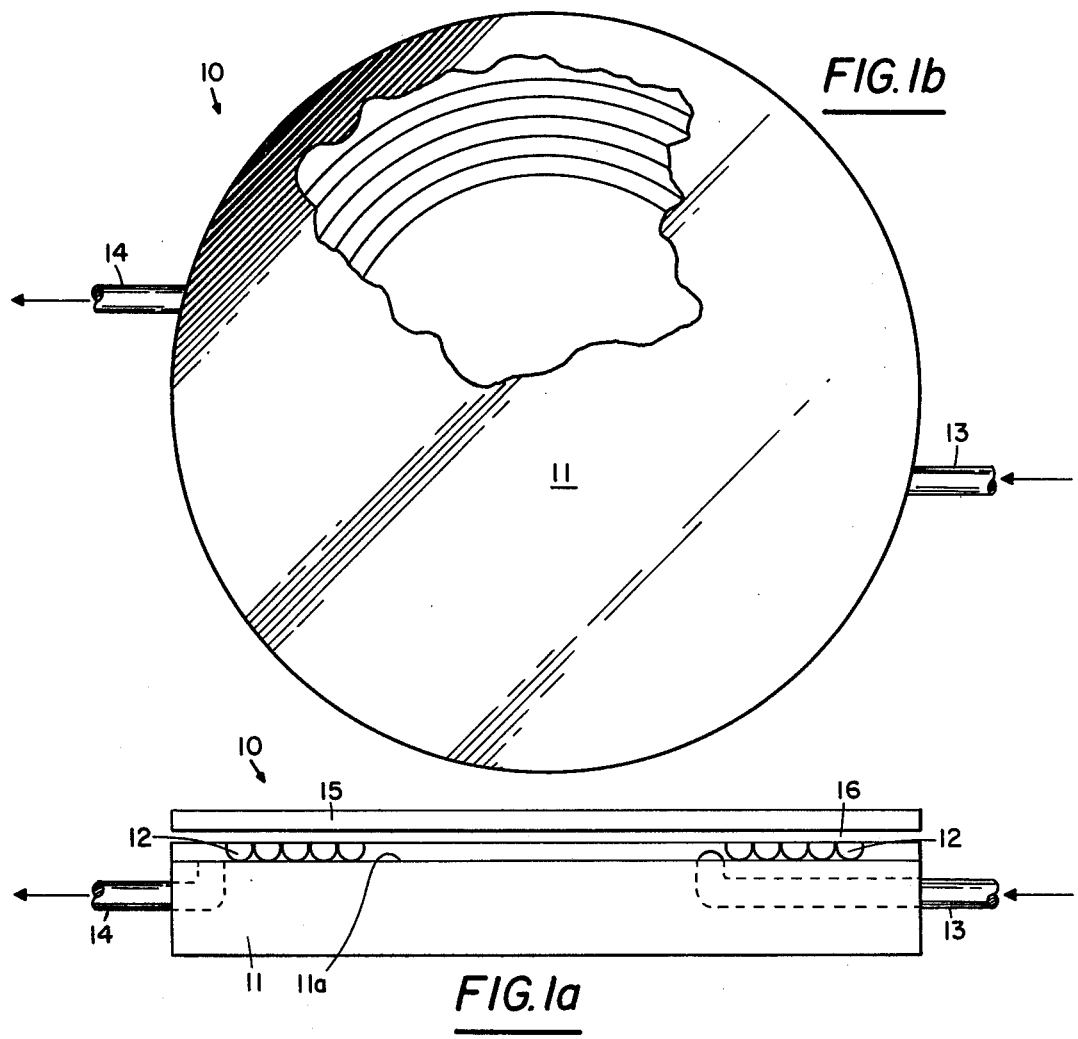
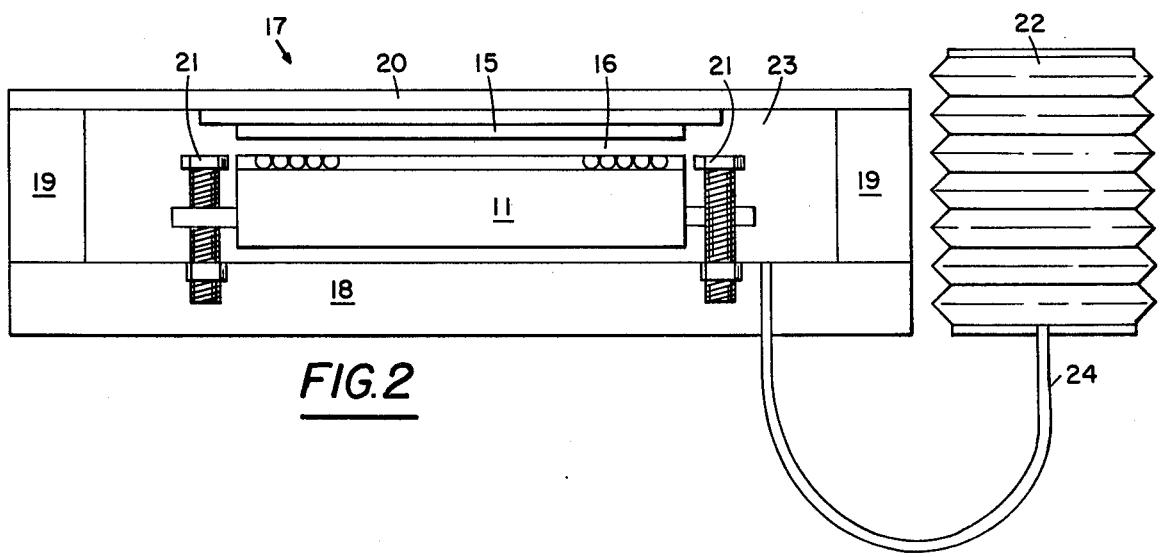

FRUSTRATED TOTAL INTERNAL REFLECTION FIBER-OPTIC SMALL-MOTION SENSOR FOR HYDROPHONE USE

BACKGROUND OF THE INVENTION

A wide variety of small motion detectors have been developed for the express purpose of sensing acoustic signals in the ocean. Generally speaking, these hydrophones have used ferroelectric, piezoelectric, etc., materials which provide representative output signals when acoustic pressure waves induce strains in them. These representative signals are fed over wires to a signal processing system. Unfortunately, the transducers usually are delicate, expensive and susceptible to electromagnetic interference.

A new family of hydrophones has been developed which rely on optical fibers. Many of these operate by sensing a change in the refractive index of the fiber as the acoustical pressure changes. The change in refractive index caused by the changes in pressure modulates the phase delay of a light beam passing through it which later is detected by means of an optical interferometer. Such is the mode of operation relied upon in U.S. Pat. Nos. 3,920,982 and 3,625,589. Although most of the problems associated with long electrical conductors and power sources are avoided and both of these devices appear to be promising, the degree of sensitivity provided may be questionable.

Thus, there is a continuing need for a hydrophone preferably relying upon fiber optic technology to provide a sensitive monitoring instrument adaptable to be operated at great depths.

SUMMARY OF THE INVENTION

The present invention is directed to providing an apparatus and method of employing a light signal to detect motion such as is produced by acoustic pressure waves. A base member has a spirally arranged optic fiber cemented on its surface. A portion of the fiber's cladding is removed to expose the core. Since the mode of light transmission through the fiber is total internal reflection, removal of the cladding exposes the evanescent optical field at the glass-to-air interface. A highly refractive plate is disposed adjacent to the optical fiber and intercepts a portion of the evanescent field when an external stimulus, such as an impinging acoustic pressure wave displaces it to thereby modulate the amplitude of the light signal passing through the optical fiber. Means are provided to provide pressure compensation to assure optimum plate positioning at changing depths and to permit varying degrees of sensitivity.

It is a prime object of the invention to provide a sensor of small motion.

Another object is to provide a sensor particularly adaptable to function as a hydrophone.

Still another object is to provide a motion sensor that avoids the problems normally associated with conventional hydrophones.

Still another object is to provide a hydrophone in which a highly refractive plate interrupts a portion of an optic fiber's evanescent field to provide indications of amplitude and frequency of impinging acoustic energy.

Yet another object is to provide a hydrophone having adjustments to compensate for various hydrostatic pressure ranges.

Still another object is to provide a fiber optic hydrophone providing for pressure compensation.

Another object is to provide a hydrophone employing a coiled optic fiber rigidly cemented onto a surface and having a portion of its cladding removed to expose an evanescent field.

Still another object is to provide a hydrophone relying on the principal of frustrated total internal reflection for giving indications of impinging acoustic energy.

These and other objects of the invention will become more readily apparent from the ensuing description when taken together with the drawings.

BRIEF DESCRIPTION OF THE DRAWINGS

FIG. 1a is a schematic representation of a cross-sectional side view of the invention.

FIG. 1b shows a top view of the invention, partially in section.

FIG. 2 shows a cross-sectional side view of a preferred application of the invention additionally including variable pressure compensation and sensitivity.

DESCRIPTION OF THE PREFERRED EMBODIMENTS

Referring now to FIGS. 1a and 1b of the drawings, an illustrative embodiment of a fiber optic small motion sensor 10 is shown in one of its less complicated forms. A rigid circular backing plate 11 has a circular surface 11a machined to present a uniformly flat area. An optical fiber 12 is cemented in a close fitting spiral pattern on the circular surface and ends 13 and 14 of the optical fiber extend outwardly through drilled passages in the backing plate.

After the fiber has been cemented onto the surface, the surface of the cement and fiber is ground and polished until a significant portion of the fiber core is exposed and made optically flat. This grinding and polishing process is well within the state-of-the-art and elaboration on this technique is unnecessary at this point.

A flat plate 15 is fashioned from a material having an index of refraction higher than that of the fiber core. The flat plate is positioned a controlled distance from, and parallel to, the polished exposed surface of the fiber optic spiral by means not shown but discussed in detail with respect to a following embodiment. The intervening space 16 between the flat plate and the surface of the coiled optical fiber is filled with air, gas, or other suitable material having a low optical loss and a refractive index lower than that of the fiber core.

When the coiled optical fiber is transmitting light from its input end 13 to its output end 14, transmission depends on total internal reflection at the air-to-core glass interface where the cladding of the fiber has been removed. Accompanying this total internal reflection is the well known evanescent field extending into space 16. This field decays exponentially to negligible proportions in a distance of the order of a wavelength of the light being transmitted. To the extent that flat plate 15 intercepts this field, total internal reflection is diminished and the excess light is coupled into the higher refractive index material of flat plate 15. This phenomenon has been referred to as "frustrated total internal reflection" in its use with totally internally reflecting prisms.

Thus, it is apparent that as the high refractive index plate 15 is made to approach the polished surface of the fiber core, the apparent transmission loss of the fiber increases. Consequently, the light passing through the fiber is modulated. Reciprocal motions of flat plate 15, small compared to one light wavelength, make significant changes in the intensity of the transmitted light and, hence, can be detected by measurement of that changing light intensity.

If the change in attenuation of a length of exposed fiber ΔL due to a change in the plate position dp is dA (in decibels), the sensitivity of the entire length L of the exposed fiber can be expressed as $$S = dA/dp \times L/dL$$

from the foregoing, it is quite clear that the maximum sensitivity to plate motion requires that the total exposed fiber length (that length of the fiber having its core exposed) be made as large as the available optical input power, unmodulated fiber loss, and detector sensitivity (not shown in the drawings but coupled to fiber optic end 14) will permit.

FIG. 2 shows how a small motion sensor, such as that described above, could be modified to function as a fiber optic hydrophone for the detection of underwater sound. Like reference characters will apply to this embodiment to identify like elements described above.

A cylindrical case 17 is made up of a relatively thick circular base plate 18, a cylindrical spacer ring 19 and a relatively thinner diaphragm 20. The highly refractive index plate 15 is attached to the diaphragm while backing plate 11 is mounted on base plate 18 of circular case 17 by means of three differential adjusting screws 21, only two of which appear in FIG. 2.

The screws are included in this embodiment to provide a fine adjustment of spacing between the backing plate 11 and the high refractive index plate 15. This modification is included to bias the motion sensor for optimum sensitivity consistent with the anticipated signal amplitude. This is to say, the plate is positioned as close to the coiled optical fiber 12 as possible without touching when sound wave amplitude peaks.

The differential adjusting screws also are used to allow the transducer to operate at a known depth by adjusting the screws to bias the sensor in advance for the expected hydrostatic pressure. However, merely adjusting the screws might compromise the sensitivity of the hydrophones since at increasing depths, diaphragm 20 would be stretched more and more.

A better alternative is to include the highly compliant bellows 22. The bellows are filled with the same fluid as space 16 and transducer cavity 23. Preferably, the fluid filling the bellow and cavity is an inert gas, although air will do. A restrictive passage 24, for example, a length of capillary tubing, connects the bellows and the cavity. Long term pressure changes result in the transfer of the fluid through the capillary tube to effect a pressure equalization on the two sides of diaphragm 20. Since the bellows is highly compliant, pressure equalization of the hydrophone is accomplished with nearly negligible deflection of the diaphragm.

The time constant resulting from the combination of the flow limitation of the capillary tube and the finite volume of the transducer cavity constitutes a low frequency cutoff on the transducer frequency response. By adjustment of the capillary tubing size and the transducer's volume, this limit can be made as low as desired. For limited depths, air should be a suitable filling material but at considerable depths, the volume required for the compliant bellows becomes impractically large. In this case, a transparent liquid such as a dielectric oil can be used as a filling.

From the foregoing it is seen that by interrupting the evanescent field along the exposed fiber optic core, modulation of the total light intensity passing through the transducer is achieved. Employing the phenomenon of "frustrated total internal reflection", provides a small motion sensor that has a wide variety of uses. Altimeters, flow meters, etc., could easily be constructed having the teachings of the present inventive concept at hand.

Obviously, many other modifications and variations of the present invention are possible in the light of the above teachings. It is therefore to be understood that within the scope of the appended claims the invention may be practiced otherwise than as specifically described.

What is claimed is:

1. An apparatus employing a light signal to detect motion comprising:
    means forming a base member;
    an optical fiber having a core of a given refractive index covered by a cladding, the optical fiber being cemented in a coiled spiral shape on the base member for transmitting light therethrough, the optical fiber having at least a portion of its cladding removed opposite the side that is cemented to the base member to create an exposed evanescent field;
    means disposed adjacent to the spiral coiled optical fiber for intercepting at least a portion of the evanescent field when an external stimulus displaces it, the intercepting means having an index of refraction higher than the core to thereby modulate the amplitude of the light signal passing through the spiral coiled optical fiber.

2. An apparatus according to claim 1 further including:
    means operatively associated with the intercepting means for maintaining it at a predetermined separation from the spiral coiled optical fiber to thereby assure the interception of at least a portion of the evanescent field.

3. An apparatus according to claim 2 further including:
    means connected to the base member for displacing it relative to the intercepting means to further assure the interception of at least a portion of the evanescent field.

4. An apparatus according to claim 3 in which the maintaining means is a gas reservoir that keeps the predetermined separation irrespective of ambient pressure variations.

5. An apparatus according to claim 4 in which the intercepting means is a high refractive plate carried on a diaphragm the plate has a high refractive index as compared to the gas next to the length of optic fiber to assure interruption of the evanescent field.

6. An apparatus according to claim 5 in which the displacing means is at least one adjusting screw mounted on the base member.

7. A method of employing a light signal to detect motion comprising:
    transmitting light through a spiral coiled light conducting member cemented onto a base member which has an exposed evanescent field emanating therefrom and
    intercepting at least a portion of the emanating evanescent field when there is a displacement of a highly refractive plate to within at least a portion of the evanescent field to thereby modulate the amplitude of the transmitted light signal.

8. A method according to claim 7 that further includes:
   stripping away at least a portion of the cladding of the spiral coiled light conducting member to expose the core and its associated evanescent field.

9. A method according to claim 8 further including: maintaining a predetermined separation between the spiral coiled light conducting member and the high refractive plate to thereby assure the interception of at least a portion of the evanescent field.

10. A method according to claim 9 further including:
    displacing the spiral coiled light conducting member relative to the highly refractive plate to further assure the interception of at least a portion of the evanescent field.

* * * * *